United States Patent [19]
Rafferty et al.

[11] 3,970,408
[45] July 20, 1976

[54] APPARATUS FOR USE WITH DELICATE FLUIDS

[75] Inventors: Edson Howard Rafferty, Excelsior; Harold D. Kletschka, Minneapolis, both of Minn.

[73] Assignee: Bio-Medicus, Inc., Minnetonka, Minn.

[22] Filed: Feb. 3, 1975

[21] Appl. No.: 546,347

Related U.S. Application Data

[63] Continuation-in-part of Ser. No. 414,225, Nov. 9, 1974, which is a continuation-in-part of Ser. No. 204,980, Dec. 6, 1971, abandoned, which is a continuation-in-part of Ser. No. 886,137, Dec. 18, 1969, Pat. No. 3,647,324, which is a continuation-in-part of Ser. No. 678,265, Oct. 26, 1967, Pat. No. 3,487,784.

[52] U.S. Cl. .................................. 415/60; 415/90; 415/DIG. 4
[51] Int. Cl.² ..................... F01B 13/00; F01B 1/36
[58] Field of Search .................. 415/64, 60, 67, 68, 415/69, 90, DIG. 4, 88, 89; 417/168

[56] References Cited
UNITED STATES PATENTS

| | | | |
|---|---|---|---|
| 862,017 | 7/1907 | Riggs | 415/64 |
| 880,327 | 2/1908 | Riggs | 415/64 |
| 3,487,767 | 1/1970 | Kristiansen | 415/77 |
| 3,635,577 | 1/1972 | Dee | 415/29 |
| 3,828,573 | 8/1974 | Eskeli | 415/88 |

*Primary Examiner*—Carlton R. Croyle
*Assistant Examiner*—Louis J. Casaregola
*Attorney, Agent, or Firm*—Merchant, Gould, Smith, Edell, Welter & Schmidt

[57] ABSTRACT

Pumps wherein smooth surfaced rotators cause propulsion of a delicate fluid without significant damage to the fluid. The pumps may be used as heart pumps, blood pumps, and pumps for all types of fluids in connection with the maintenance of life or biological functions in a human or animal subject in many in vivo, ex vivo, or in vitro applications, or for any other application requiring gentle fluid handling. The pumps may be actuated by internal or external electric motors, and the rotators may be configured to converge mutually as an inverse function of distance from the axis of the rotators. The rotators may be connected together, by pins passing through the fluid passages, for mounting and driving as a unit, or may be mounted and driven independently to further eliminate the possibility of damage to the fluid by rotator-connection members.

10 Claims, 9 Drawing Figures

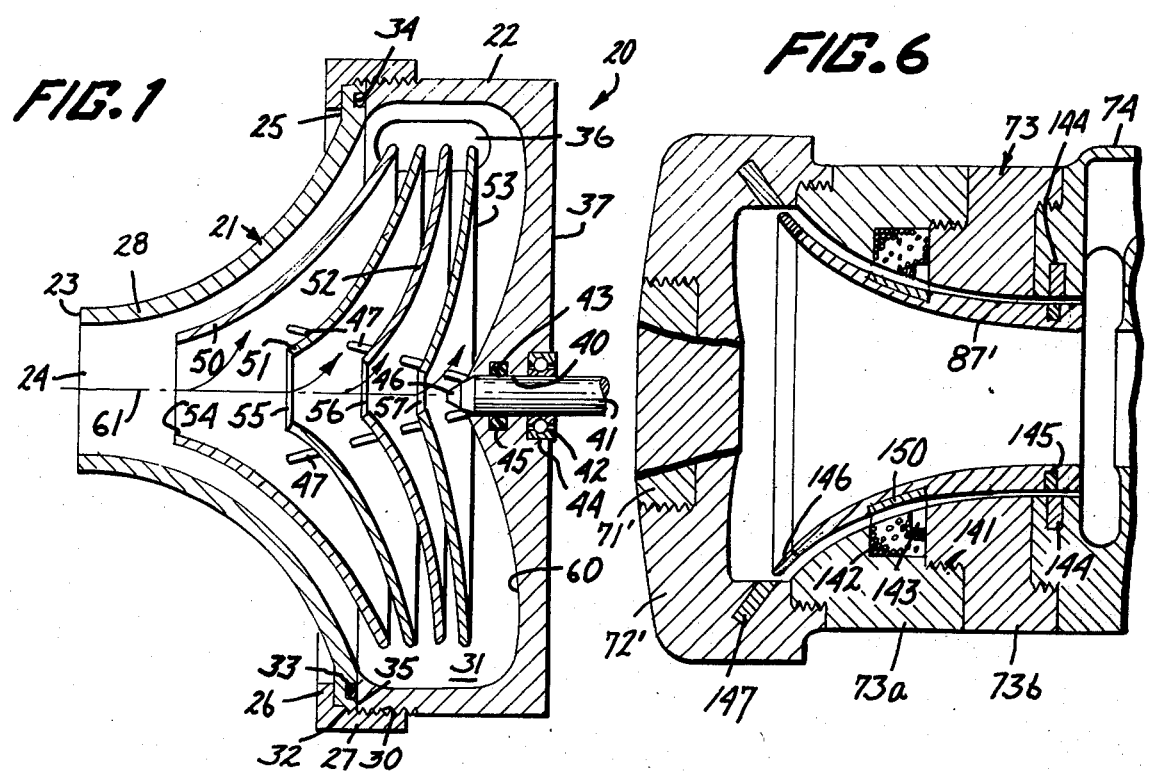
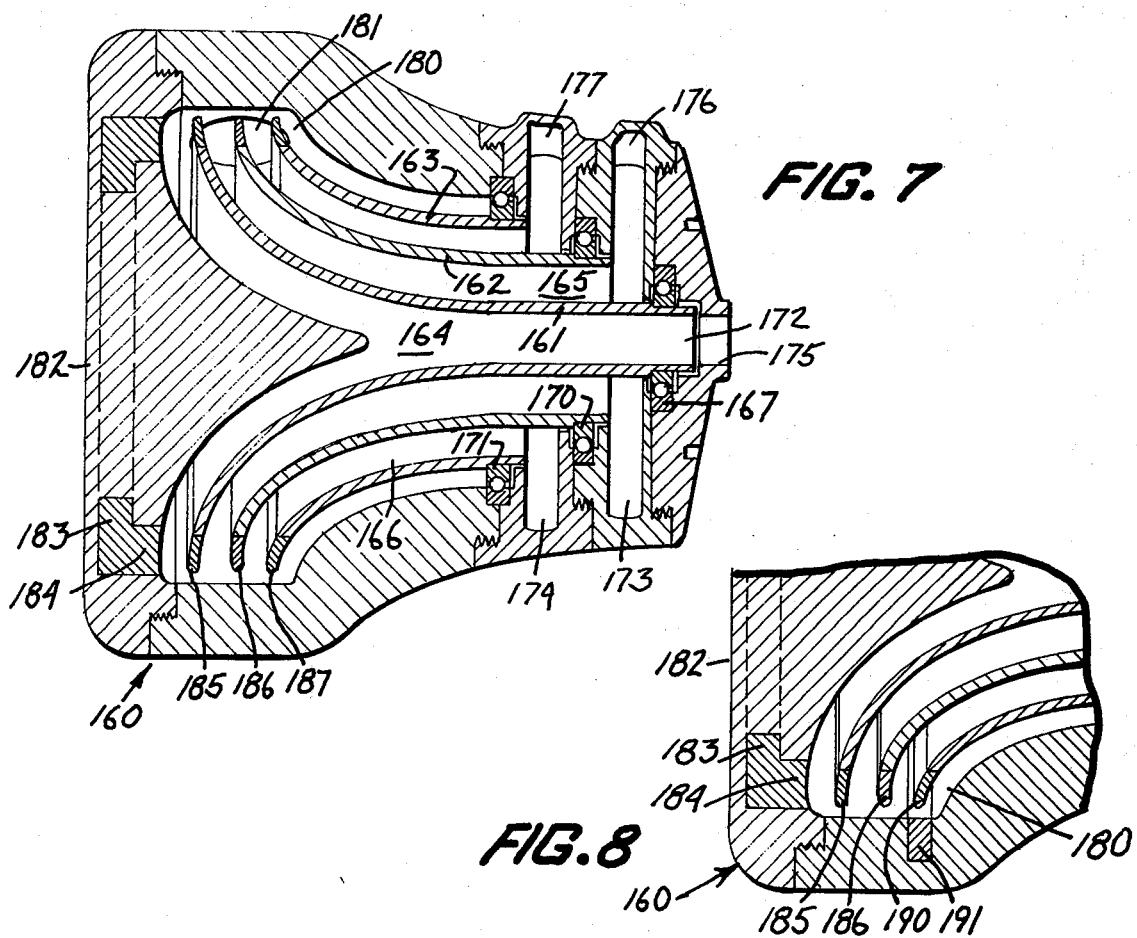

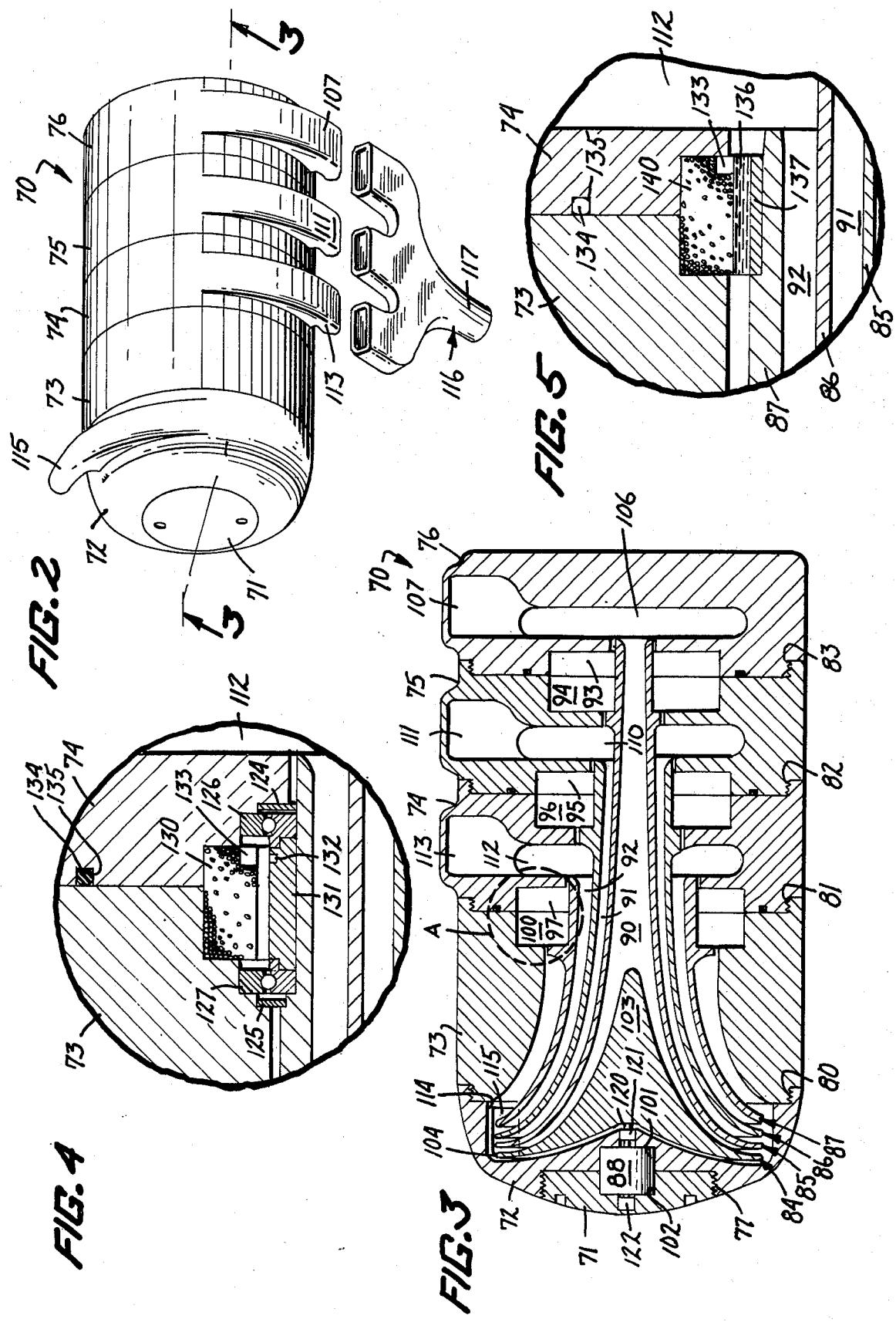

APPARATUS FOR USE WITH DELICATE FLUIDS

This application is a continuation-in-part of application Ser. No. 414,225, filed Nov. 9, 1974, which is a continuation-in-part of application Ser. No. 204,980, filed Dec. 6, 1971 (now abandoned), which is a continuation-in-part of application Ser. No. 886,137, filed Dec. 18, 1969 (now U.S. Pat. No. 3,647,324), which in turn is a continuation-in-part of application Ser. No. 678,265, filed Oct. 26, 1967 (now U.S. Pat. No. 3,487,784).

BACKGROUND OF THE INVENTION

FIELD OF THE INVENTION

The field of the invention is that of pumping apparatus, and particularly apparatus used for pumping the blood of a living person, or of a living animal, to replace one or more pumping functions of the human or animal heart in case of disability thereof. The heart replacement may be partial or complete, temporary or permanent. While pumps according to the invention are primarily for pumping blood, they may be employed in other instances for pumping other materials. The pumping equipment provided by the invention has accelerators for the fluid to be pumped, herein called rotators, which rotate to impel the fluid circularly at substantially the speed of the rotators. The pumps are particularly adapted for the pumping of blood and other delicate fluid materials, biological and non-biological in nature, or for any other application requiring the gentle handling of a fluid, suspension, precipitate or liquid-solid mixture, without any significant damaging effect on the blood or other material being pumped. The pumps do not impose sudden pressure changes, impacts, or rapid changes in direction of flow, and thus do not cause significant injury to or destruction of the pumped material and its components.

Artificial heart pumps generally have been of the positive displacement type, to cause pulsating flow of the fluid being pumped. Although a pulsating movement of the blood through the body may not be necessary to sustain life, the prior art has, nevertheless, not afforded a solution to the problems involved in utilization of centrifugal pumps for pumping blood. This invention solves these problems by providing rotary pumping means, for pumping blood or other delicate fluids, which produce minimum levels of shear and turbulence, thus eliminating any significant damage to the fluid and its components as a result of the pumping.

SUMMARY OF THE INVENTION

The invention is of rotary pumps which are suitable for use as heart pumps or blood pumps, as pumps for all types of fluids in connection with the maintenance of life or biological functions in a human body or animal body, or in any other pumping function. The pumps can be used to replace or assist the pumping functions in a human body or animal body, or in any other pumping function. The pumps can be used to replace or assist the pumping functions of the heart in vivo or ex vivo. The pumps can be used to pump biological fluids in vitro or in any in vivo, ex vivo, and in vitro combination. The pumps may also be used to pump non-biological fluids as well. The non-biological fluids so pumped may be pumped in connection with biological or non-biological activities, functions or applications.

The pumps according to the invention are rotary devices having smooth accelerators or rotators defining passages through which the fluid to be pumped is caused to flow outwardly from the axes of the rotators, which preferably have a constant angular velocity. The rotating rotator surfaces cause the fluid, introduced at or near the rotator axis, to move substantially circularly around the rotator axis, the movement having minor components along the axis and radially outward, by which minor components it differs from the purely rotary movement of the rotators. Although the angular velocity of the fluid is substantially constant as it moves outwardly, its linear velocity continuously increases as the radial distance from the axis increases. In order to preserve the flow patterns through the pumps, the rotators may be designed to converge mutually toward their outer edges, so that while the rotator passages remain constant in cross sectional area, the spacing between them varies as an inverse function of radial distance from the rotator axis. This prevents effects in the fluid, such as cavitation, pressurization, depressurization, and the like, from occurring inside the pump passages, thereby preventing shock and damage to the fluid being pumped.

when used as pumps, the rotator or rotators may be arranged for driving by a discrete motor, or the motor may be integrated directly into the pump structure. When a plurality of rotators is used, they may be driven by a single motor and interconnected by members around which the pumped fluid passes, in which case we prefer that their cross sections be streamlined to minimize physical interaction with the fluid, or they may be separately mounted for rotation, driven by separate motors, and supplied separately with the fluid to be pumped. This arrangement removes any possibility of blood defibrination, or of partial stoppage of a passage by a solid component of the fluid trapped at a cross member.

Pumps according to the invention may be used in pumping blood for circulation through the cardio-vascular system of a living person or animal, or for pumping blood through natural or artificial organs such as kidneys or lungs. They are adaptable for use implanted within a body cavity, as replacements for any or all of the pumping functions of the heart, and may also be used externally of the body of a subject. The pumps are designed to operate without producing severe pressure changes, physical impacts, sudden direction changes, and the like, so that none of the fluid components are subjected to treatment which will damage them for their normal use. They do not require the use of valves, such as those of the biological heart, but valves may be provided if desired, particularly in the heart-assist-type usage.

The pumps are useful in both biological and nonbiological applications. They could, for example, be used to propel a motorboat, the pumps being very quiet and of low turbulence, in centrifuging apparatus, as infusion pumps, as suction pumps (for chest tubes, for example), as aspiration devices (to suction out blood from the operative field in an atraumatic fashion so that the blood might be reused in order to save on blood transfusions, and so forth), to pump water from boats, for fountain sprays and garden waterfalls, for pumping slurries such as sewage, for pumping paints, foods, or suspension of metal particles, and for many other uses including, but not restricted to uses where gentle handling of the fluid may be desired.

Various advantages and features of novelty which characterize our invention are pointed out with particularity in the claims annexed hereto and forming a part hereof. However, for a better understanding of the invention, its advantages, and objects attained by its use, reference should be had to the drawing which forms a further part hereof, and to the accompanying descriptive matter, in which there are illustrated and described certain preferred embodiments of the invention.

BRIEF DESCRIPTION OF THE DRAWING

In the drawing,

FIG. 1 shows an embodiment of the invention in central section;

FIG. 2 is an elevation of another embodiment of the invention;

FIG. 3 is a section taken along the line 3—3 of FIG. 2;

FIG. 4 is an enlarged showing of the area indicated by the circle "A" in FIG. 3, giving mounting and driving details;

FIGS. 5 and 6 are showings like FIG. 4 of further modified mounting and drive structures, the latter having parts omitted or broken away for clarity of illustration;

FIG. 7 is a longitudinal section of another pump embodying the invention;

FIG. 8 is a fragmentary showing of a modification of the structure of FIG. 7.

DESCRIPTION OF THE PREFERRED EMBODIMENTS

Figure 9:
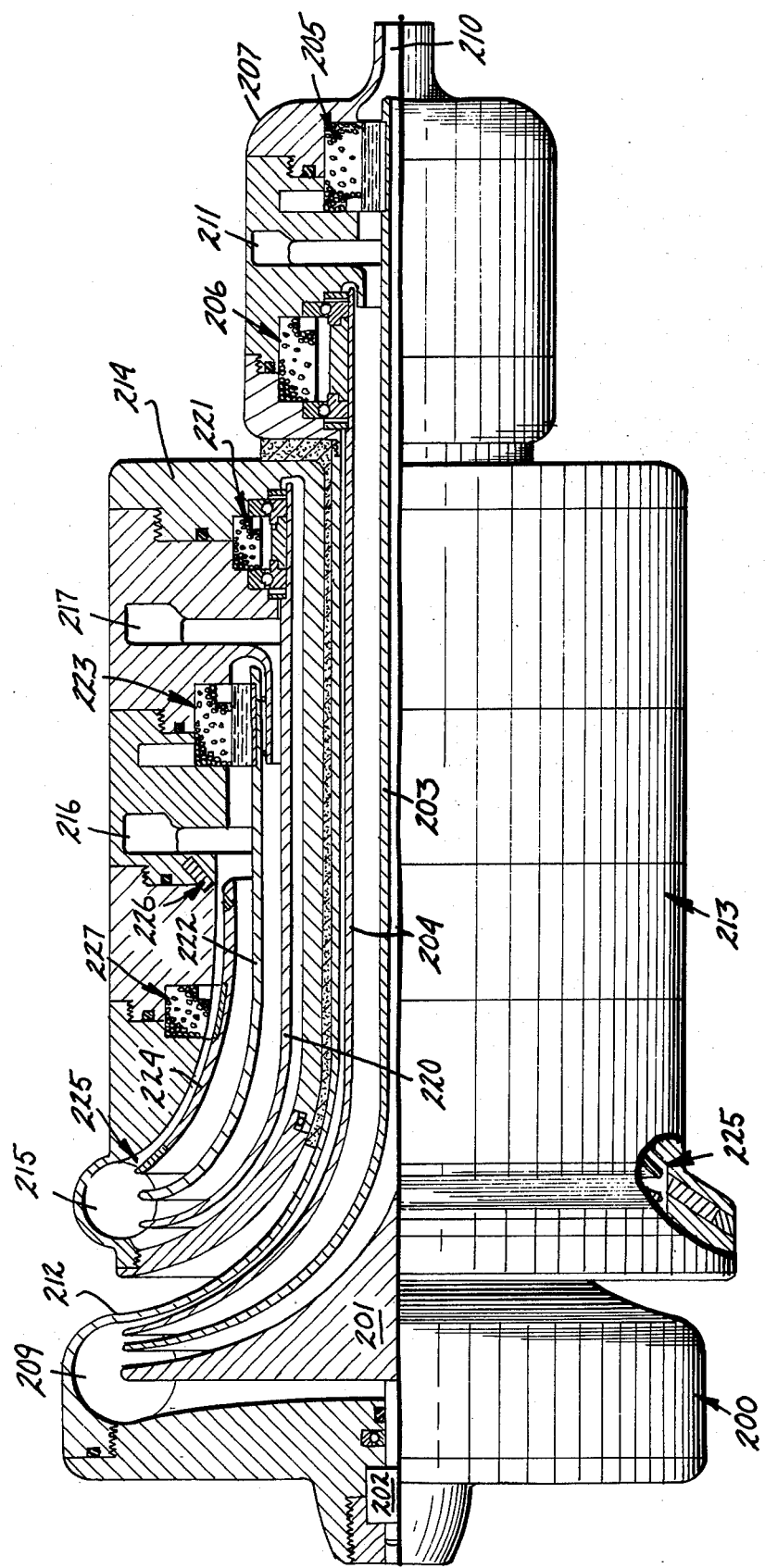
FIG. 9 is a longitudinal sectional view of a concentric double pump embodying this invention.

The pumps will be described with blood as the fluid being pumped, since that is the primary purpose for which pumps according to the invention have been developed, but it is to be understood taht the pumps will be useful for all of the uses and purposes mentioned in the disclosure, and the description may be applied to such uses and purposes.

Blood is a complex and delicate fluid. It is essentially made up of plasma, a pale yellow liquid containing microscopic materials, and the "formed elements" which include the red corpuscles (erythrocytes), white corpuscles (leukocytes), and platelets (thrombocytes). These and the other constituents of blood, as well as the nature of suspension of these materials in blood, are fairly readily affected by the manner in which blood is physically handled or treated. Blood subjected to mechanical shear, to impact, to depressurization, or other forces, may be seriously damaged. In addition, the balance between the blood constituents may readily be affected. Commencement of deterioration may result from physical mishandling of blood. Blood which has been damaged may be unfit for use.

The heart propels or pumps blood through the body in a circulating, cyclic fashion. The blood passes repeatedly through the heart. A pump for replacing one or more pumping functions of the heart should, therefore, be capable of repeatedly pumping the same blood, time and time again, without damaging the blood, at least not beyond the extent to which the body can accomodate by repairing or replacing the blood components or eliminating damaged or waste materials therefrom.

Blood also contains dissolved and chemically combined gases, which may be seriously affected by improper physical handling of the blood. It has, for example, been established that subjecting blood to negative or sub-atmospheric pressures of, say, minus 300 millimeters of mercury, is detrimental not only to the blood cells, which may rupture, but to the body due to the release of dissolved gases from solution, even when the reduced pressures are only temporary.

The blood pressure is the pressure of the blood on the walls of the arteries, and is dependent on the energy of the heart action, the elasticity of the walls of the arteries, the peripheral resistance in the capillaries, and the volume and viscosity of the blood. The maximum pressure occurs at the time of the ventricular systole of the heart and is termed maximum or systolic pressure. The normal systolic pressure may be from about 80 millimeters of mercury (mm. Hg) to about 150 mm. Hg, the pressure ordinarily increasing with increasing age. Pressures somewhat outside this range are not uncommon. The minimum pressure occurs at the ventricular diastole of the heart and is termed minimum or diastolic pressure. The diastolic pressure may be about 30 to 50 mm. Hg lower than the systolic pressure.

The preferred embodiments of the invention shown and described have in common that the blood or other fluid is handled gently, without shear, shock, vibration, impact, severe pressure or temperature change, or any other condition or treatment which would unduly damage the blood or other fluid. Essentially nonturbulent flow is maintained through the pumps, and the pumped fluid is accelerated gradually and smoothly.

The pumping action obtained may be described as radially increasing pressure gradient pumping, or in some cases more specifically as constrained force-vortex radially increasing pressure gradient pumping. In centrifugal pumps, the fluid acted on by the vanes of the impeller is positively driven or thrown outwardly (radially) by the vane rotation. The fluid as it moves from the vanes to the ring-shaped volute space beyond the tips of the vanes is reduced in velocity, and as the velocity decreases the pressure increases according to Bernoulli's theorum. Handling of many delicate fluids, such as blood, in this fashion would destroy them for use.

On the contrary, in the pumps provided according to this invention, the pumped fluid is not driven or thrust all but instead is constrained to circulate in the pumping chamber with increasing velocity as it moves farther and farther from the center. At the outer periphery of the accelerator or rotator, the velocity of the fluid is maximum.

The action of the fluid in the pumps may be clarified by analogy to a glass of water turning about its vertical axis without sideways motion or wobble. Because of its contact with the sides and the inherent potential shear force of the water in the glass, the water will rotate in the form of a force-vortex without much slip or shear between radially adjacent particles of water, and the water radially away from the center of rotation will be moving faster than water nearer the center. If water is introduced through a tube at the axis of the glass and water is removed through one or more holes through the side of the glass and the water in the glass is constrained by capping off the top of the glass, water will be pumped by the rotation of the glass. In the pumps afforded by this invention, while rotators are provided in a number of different forms, the rotators are designed so that they act to increase the velocity or swirling speed of the fluid passing through the pumps, but do not act to drive or throw the fluid toward the periphery or volute of the pump chamber, but instead only increase the rotational speed of the fluid. As the velocity of the fluid is increased, it moves toward the periphery of the chamber.

Referring now to FIG. 1, there is shown a pump 20 having a housing in two parts 21 and 22. Housing 21 is flaringly enlarged along a wall 28 from one end 23 around a fluid inlet 24, and has a flat surface 25 around its outer edge to engage the flange 26 of a ring-nut 27 which extends beyond the end of the housing and is internally threaded at 30. Housing part 22 has a central cavity 31 and is outwardly cylindrical with external threads 32 around its open end on to which nut 27 is screwed to secure the two parts of the housing together. A seal 33 is disposed in a groove 34 around the annular end 35 of part 21 to make the connection leak-proof.

In FIG. 1, as in the other figures, the equipment is shown in schematic form and not to any particular scale. A tangential outlet port 36 is provided in the side wall of housing part 22. At the center of the closed end 37 of housing part 22, an opening 40 is provided to receive a shaft 41, journaled in a bearing 42, and surrounded by a seal 43, the bearing and seal being disposed in annular enlargements 44 and 45 respectively around the shaft opening. Shaft 41 is mechanically connected to any suitable driving motor, not shown.

End wall 37 is inwardly thickened towards its center. The inner end 46 of shaft 41 is of conical shape and a plurality of small diameter rods 47, preferably 3 in number, extend obliquely from the shaft end at equal angles and are equally spaced around the axis of the shaft. A plurality of smooth accelerators or rotators 50–53 of different flared curvatures are supported by the rods 47. The rotators 50–53 have holes therethrough to receive the rods 47, rotator 50 being positioned at the ends of the rods, and rotators 51–53 being spaced between rotator 50 and the end of shaft 41 so that the rotators are coaxial and telescoped or nested axially. The rotators are fixed to the rods by press-fitting, or by any other suitable means, and are configured so that the spacings therebetween decrease outwardly from the axis of shaft 41.

The rotators 50–53 flare outwardly from left to right as seen in the figure, and have circular central openings 54–57 of sequentially smaller size in the same direction. The spacing between rotators 50 and 51 is larger than the spacing between rotators 51 and 52, which is larger than the spacing between rotators 52 and 53. The unequal peripheral spacings of the rotators are required by the more sharply flaring shapes of earlier rotators, e.g., rotator 50, as compared with later rotators, e.g., rotator 51.

In order to avoid undesirable damage to the fluid by such effects as cavitation, pressurization, and depressurization it is desirable to maintain a uniform flow regimen through the pump passages separated by the rotators. This can be accomplished, for the passages where both walls are formed by moving rotators, by varying the cross sectional areas of the several passages as inverse functions of radial distance from the axis. As shown in FIG. 1, rotators 50, 51, 52 and 53 converge outwardly so that the area of the annular passages is in each case substantially uniform throughout its extent.

The spacings between the walls 28 and 60 and the rotators 50 and 53 adjacent thereto, however, are designed to increase outwardly rather than to decrease. The reason for this is that, because the housing walls do not rotate, and because the fluid velocity increases with distance from the axis, the shear in the fluid increases to undesirable levels if the end passages converge or are even uniform. Therefore, in order to maintain low shear forces in the liquid circulating in the passages next to the fixed walls, the passages are arranged to diverge outwardly.

The operation of this embodiment of the invention is as follows. Housing 20 is connected so that the blood or other fluid to be pumped is supplied at 24, and the pump outlet at 36 is connected to a point of use for the fluid. When shaft 41 is driven, rotators 50 and 53 begin to rotate in contact with the fluid and cause it to rotate about the common axis and also to move axially to the right and radially outward, as seen in FIG. 1, some fluid being expelled from the pump at 36 as more is drawn in at 24. Input to this pump is axial, while output from the pump is tangential. When the fluid flows in through inlets 24 it is divided as it moves to the right, as shown by the branched arrow 61 in FIG. 1. The central openings 54–57 are sized to receive the flow remaining at later rotators after partial flow has been earlier diverted.

By reason of the smoothness of the rotator surfaces and the fact that the fluid movement is substantially the same in speed and direction as the movement of the rotators, no significant damaging forces act on or in the fluid. The pump may thus continue to operate and recirculate the fluid for very considerable lengths of time without exercising a significant degrading effect on the fluid.

It was mentioned above that members 47 of FIG. 1 are so small and so streamlined, and that the relative velocity of the fluid with respect to the rotators is so small, that the members cause only insignificant impact or turbulence damage to the fluid being pumped. The structure of FIGS. 2–4 is designed to reduce even this slight effect, by entirely eliminating any members extending across the various passages transversely to the flow of the fluid. It also minimizes the likelihood that any solid bodies carried in a fluid being pumped may be trapped behind some cross member.

FIG. 2 shows this embodiment of the pump to comprise a housing 70 made up of a plurality of portions 71, 72, 73, 74, 75 and 76 of generally circular outline, secured together along a common axis as by the threaded connections 77, 80 81 82 and 83 of FIG. 3. Contained within the housing are a plurality of nested, coaxial, flared rotators 84, 85, 86 and 87 which comprise the moving walls of a plurality of pumping passages 90, 91 and 92. As shown schematically in FIG. 3, the rotary mounting and driving means for rotator 85 is contained in aligned chambers 93 and 94 in housing portions 76 and 75 respectively, the rotary mounting and driving means for rotator 86 are contained in aligned chambers 95 and 96 in housing portions 75 and 74, the rotary mounting and driving means for rotator 87 are contained in aligned chambers 97 and 100 in housing portions 74 and 73, respectively, and the rotary mounting and driving means for rotator 84 are contained in aligned chambers 101 and 102 of housing portions 72 and 71 respectively.

Rotators 85, 86 and 87 are hollow, elongated members flaring outwardly from right to left as seen in FIG.

3, and supported and driven at their smaller ends for rotation about a common axis: rotator 87 has an outer surface which is spaced from housing portion 73. Rotator 84 is shown as solid, and as flaring from an inner tip 103 to an enlarged rim 104: it is supported and driven for rotation about the common axis, by suitable motor and driving means 88 and has a surface which is spaced from housing member 72. The inner surface of rotator 87, the outer surface of rotator 84, and both surfaces of rotators 85 and 86 are smooth. Housing portion 76 has a chamber 106 which communicates with chamber 90, and is provided with a tangential inlet 107. Housing portion 75 has an annular chamber 110 which communicates with chamber 91, and is provided with a tangential inlet 111. Housing portion 74 has an annular chamber 112 which communicates with chamber 92, and is provided with a tangential end at 113. Housing portion 72 has an annular chamber 114 which communicates with the large ends of rotators 84, 85, 86 and 87, and is provided with a tangential outlet 115. Inlets 107, 111 and 113 are connected to a manifold 116 as shown in FIG. 2, having a inlet connection 117. Connections 117 and 115 are the inlet and outlet connections for the pump.

As shown in FIG. 3, rotator 84 is mounted on a shaft 120 carried in bearings 121 and 122 and driven by a suitable motor 88. The structure enclosed in the circle "A" and shown schematically in FIG. 3 may be as illustrated in more complete detail in FIG. 4. Elements 124 and 125 are sealing members, and elements 126 and 127 are bearings. The stator of a permanent magnet DC motor is shown at 130, and the magnetic rotor is shown at 131. Stator 130 may be energized through conductors leading outside the housing, or may be connected to a battery embedded in the housing: the necessary commutation may be controlled by means including phosphorescent spots carried by rotator 131 as suggested at 132, in combination with light sensitive means 133 associated with stator 130. Alternatively, Hall effect sensing means may be used at 133 to cooperate with magnetic rotor 131 in controlling the commutation of stator 130.

To assemble the structure, seal 125 is first inserted in housing portion 73, followed by bearing 127 and stator winding 130. Seal 124 and then bearing 126 are inserted in housing portion 74. Rotor 131 is placed in housing portion 73 and rotator 87 is inserted through bearing 127 and rotor 131: housing portion 74 is now screwed into portion 73, bearing 126 and seal 124 thus taking their places around rotator 87. Rotator 87 may be a press fit in rotor 131 and bearings 126 and 127, or may be adhesively secured therein. An O-ring 134 in a groove 135 completes the seal between the housing portions.

It will be appreciated that structures like that just described may also be used to support and drive rotators 86 and 85 if desired. Alternative structures within the teaching of the invention may also be used. In FIG. 5, for example, one such alternate is shown in which a ferro-magnetic fluid 136 between the rotor 137 and the stator 140 of the driving motor acts both as a bearing and as a seal. In this modification, the photoelectric regulation of stator commutation is not appropriate, but magnetic regulation by Hall effect sensing means 133 may be used.

FIG. 6 is a fragmentary showing of a further modified arrangement for driving and magnetically supporting or "levitating" a single rotator, especially useful in connection with outer rotator 87'. In this structure, housing portion 73 is divided into two portons 73a and 73b screwed together at 141, and containing a stator winding 142 with Hall effect sensing means 143. Housing porton 74 has molded or otherwise secured therein a structure 144 of permanent or electromagnets which provides an annulus of inwardly directed magnetic poles, all of the same polarity, north for example. Rotator 87' has at its smaller end a permanent magnet in the form of a ring 145 whose outer edge is in this case everywhere of north magnetic polarity while its inner edge is of south magnetic polarity. At its large end, rotator 87' carries a second permanent magnet in the form of a ring 146 whose outer edge is of a first magnetic polarity, south for example, while its inner edge is of north polarity. Housing portion 72' contains a magnetic structure 147 of permanent or electromagnets which then provides a second annulus of inwardly directed south magnetic poles. Thus, at each end of rotator 87' there is an annular pair of magnetic fields of the same polarity, which repel each other around the entire periphery of the rotator. As a result of these fields, rotator 87' is carried in a magnetic bearing at each of its ends, which bearings also act axially in the rotator to retain it in its desired axial location since the repulsions exerted by the poles become greater as the rotator moves incrementally out of its desired position in any direction.

The rotor which cooperates with stator 142 to drive rotator 87' is carried in or on the rotator at 150.

The embodiment of the invention shown in FIG. 7 is also free from members or struts interconnecting the rotators and traversing the passages through which the fluid passes, but is arranged to drive all the rotors from a single stator. The figure is highly schematic, and shows a housing 160 containing a plurality of rotators 161, 162 and 163 which are nested to define a plurality of pumping passages 164, 165 and 166. The rotators are mounted, for rotation about a common axis, by any suitable means such as bearings 167, 170 and 171 cemented or otherwise secured in the housing and to the rotators. Passages 164, 165 and 166 open at the smaller ends of the rotators into annular chambers 172, 173 and 174 having inlet ports 175, 176 and 177, all respectively, for the ingress of the fluid to be pumped. The port for passage 164 is shown as axial, while those for passages 165 and 166 are shown tangential. Fluid may be supplied to ports 175, 176 and 177 from a suitable manifold not shown.

All the passages open at their larger ends into an annular chamber 180 having a tangential outlet port 181. The end 182 of housing 160 remote from the inlet ports may be a removable cap having in inner surface with a contour projecting to complete the configuration of passage 164. Molded into or otherwise secured to cap 182 are the laminations of a stator winding 183 having salient poles 184 projecting inwardly toward the rotors, and energized in any suitable fashion as by conductors leading out through the cap, or by an embedded battery.

The periphery of the large end of rotator 161 has secured thereto or embedded therein a magnetic rotor 185 which cooperates with stator 183 to comprise a DC motor, the magnetic axis of the rotor being parallel to the axis of rotation of the rotator. Similar magnetic rotors 186 and 187 are provided at the peripheries of rotators 162 and 163, the magnetic axes being aligned and the polarities being the same. The rotators are thus magnetically coupled, and when stator 183 is appropriately energized by any suitable commutating arrangement, rotor 185 causes rotation of rotator 161, and the other two rotators are inductively driven thereby.

FIG. 8 shows a slight variation in the structure of FIG. 7. Here the magnetic rotor 190 at the periphery of rotator 163 does not have its magnetic axis aligned with those of rotators 185 and 186, but rather aligned radially to cooperate with a separate stator 191 carried by housing 160. Thus, even when the drive is applied to the rotators at their larger ends it is possible to have individual motors if this appears desirable.

Any of the pumps as described above can be designed to perform the functions of the left heart or those of the right heart: obviously, if the total heart is to be replaced, a pair of pumps is required, each designed appropriately for its intended function. A highly desirable form of such a double pump is shown schematically in FIG. 9, wherein the two individual pumps are designed for coaxial interrelation, one surrounding the other. Thus, a first, inner pump 200 has a rotator 201 pivoted and driven at 202, and two further rotators 203 and 204 pivoted and driven at 205 and 206 in a housing extension 207 having input ports 210 and 211. The principal housing 212 of this pump is of generally cylindrical configuration and of relatively small diameter: its output port is shown at 209.

The housing 213 of the second pump 214 is in the form of a hollow cylinder. The pump has an outlet port 215 and a pair of inlet ports 216 and 217. In this pump a first rotator 220 is mounted and driven at 221, a second rotator 222 is mounted and driven at 223, and a third rotator 224 is levitated at 225 and 226 and driven at 227. The mounting and drive details of both of these pumps are as fully described above in connection with FIGS. 3, 4, 5, and 6, except that the stationary pole structure at 225 is interrupted to pass the outlet port 215.

While the structure of FIG. 9 shows an assembly to two pumps coaxially arranged, it will be realized that when more than two concurrent pump functions are necessary, the principle of FIG. 9 may be extended to comprehend a further pump, and also that our pumps are well adapted for use in clusters of three or even more, in situations where lateral space is more readily available than axial space.

It will be seen that the blood or other fluid passing through any of these pumps is not subjected to any substantial agitation by the rotation of the rotators, of whichever form, or by any other portion of the pump apparatus. There are no sudden changes in direction of the flow through the pumps, all joints between surfaces being smooth and all surfaces over which the fluid flows being smooth.

The spacing between the outer peripheral edges of the rotators may be very close, i.e., a few thousandths of an inch, or may be larger. Inwardly of the rotator outer edges, the spacings may become increasingly larger. Close peripheral spacings do not cause unacceptable damage to blood but do enable the pump to work efficiently. The efficiency of the pump is directly related to the transfer efficiency of the rotators which is a function of the rotator spacing. There exists an optimum spacing for each set of rotators. Therefore, by using the "optimum" spacing, it is possible to optimize the pump efficiency. However, if the close spacings are maintained over a considerable radial extent, then excessive damage to blood or other fluid may occur. The majority of the spacing effect on efficiency takes place at the largest radii, and thus, close spacing need only be maintained at the periphery. Therefore, the rotators can be made with the continuously outwardly decreasing spacings as herein described and, thus, low fluid damage and high pumping efficiency can be combined.

It will be realized that pumps may be supplied according to the invention with any number of pumping stages, and may include individual pumping stages of any of the types mentioned herein in any combination.

In each of the pumps it will be noted that the rotators are designed to avoid turbulence, to avoid rapid pressuring and depressuring of the blood or other fluid being pumped, and also to avoid any physical grinding or abrasive action upon the fluid. As has been made clear, these rotator designs are made in this manner in order that blood or other delicate fluids being pumped, some containing solids or gases in suspension, will not suffer detriment and will not be destroyed by the pumping operation.

The convergence of the rotators, with diminution of the flow space therebetween outwardly, prevents cavitation (dissolved gases coming out of liquid solution to form bubbles because of the pressure reduction within the pumps), which would adversely affect pumping efficiencies and cause damage to certain fluids, such as blood. The convergence of the rotators may be such that the flow rate either somewhat increases outwardly or somewhat decreases outwardly, with corresponding pressure changes on the fluid being pumped. In the outer annular flow spaces between the rotators maximum fluid velocity is maintained so that conversion of velocity to pressure occurs at the outer pump housing and as fluid enters the pump outlet.

In contrast to centrifugal pumps, the revolutions per minute of the rotators employed with the pumps herein shown and described are designed to be kept minimal. The several rotator designs presented are each of a form adapted to progressively increase the circular fluid velocities as the rotator turns and as the fluid advances toward the periphery of the rotator. In each pump presented, the annular fluid circulation space is almost entirely unobstructed and regular so that fluid can circulate therein without turbulence or baffle effects. The connecting struts, which are kept as small as possible where used, provide the only exception to this. These struts are also kept as close to the center of rotation as possible to minimize their velocities.

As hereinbefore indicated, pumps may be made according to the invention incorporating features from one or more of the preferred embodiments shown and described herein, any particular feature not being confined to use only with the other features in connection with which it is herein shown and described.

The pumps and their parts may be constructed of any materials compatible with their intended use, including metals, mineral materials, plastics, rubbers, wood, or other suitable materials. When blood is to be pumped, consideration must be given to biological compatibility so that damage to the blood will not result. Low temperature isotropic carbon and certain polymers or rubbers have been successfully used in contact with blood, and may be used in construction of the pumps for blood pumping adaptations. Non-corrosive metals and alloys may be used in the pumps where required.

The housing and rotators may be constructed of suitable material so that the housing may be rigid, semi-rigid, or elastic in whole or in part. The non-rigid constructions can be used for imparting a pulsed characteristic to blood in heart simulation pumps.

While the rotators shown herein may in some cases perform better when rotated in one direction, it should be understood that they may be rotated in either direction, or may vary in rotational velocity and direction, i.e., reversed, without other modification of the pumps. Each of the rotators presents surfaces to the fluid being pumped, to cause accelerating circular fluid motion in the pumping chamber. In some cases, the surfaces are parallel; in other cases non-parallel surfaces are provided, the non-parallel surfaces being either outwardly convergent or otuwardly divergent in accordance with the exigencies of the particular application. Each of these surfaces, of whatever form will accelerate the fluid regardless of the direction of rotation of the rotator. Each rotator should be rotated at a speed such that essentially no fluid turbulence occurs, and differences in the rotator designs affect the maximum speed at which a particular rotator may be rotated. The physical and flow properties of the fluid pumped will, of course, also affect the maximum speeds of rotation at which the rotators may be operated without turbulence and other objectionable effects, such as cavitation, vapor binding, and the like. It is, therefore, not possible to set forth exact rotational speed ranges for the rotators. As internally placed heart pumps, the pumps may be as large as four inches in diameter, and, with removal of a lung, even larger.

According to the precepts of this invention, the forms of the rotators may vary considerably. For example, the rotators may be constructed entirely or partly of porous or perforate materials, i.e., the rotators which accelerate the fluid circularly may be made of screen, of perforate plates or sheets, of spaced rods, or the like, and will still ably perform their fluid accelerating function. They may also be constructed out of solid or non-porous materials. Rotators may be of axially extended form, so that the fluid is accelerated axially or axially and radially. Designs of this nature extend the flowpath from inlet to outlet so that acceleration is at a slower rate. In multi-stage pumps, the several rotators, which may be alike or unlike, may be driven at different rotational speeds. The axes of multi-stage rotators may be offset and in other positions out of strict alignment.

While preferred embodiments of apparatus according to the invention have been shown and described, many modifications thereof may be made by a person skilled in the art without departing from the spirit of the invention, and it is intended to protect by Letters Patent all forms of the invention falling within the scope of the following claims.

What is claimed is:

1. In rotary pumping apparatus for generating flow with an axial component, in combination:
   1. a first bladeless pump structure including means mounting and driving at least one elongated pumping member for rotation about a first axis to cause fluid flow along said axis;
   2. a second, bladeless hollow pump structure including means mounting and driving at least one elongated pumping member for rotation about a second axis to cause fluid flow along said axis; and
   3. means mounting said first pumping structure within said second pumping structure so that said first and second axes coincide and said fluid flows are in the same direction.

2. In rotary pumping apparatus for generating flow with an axial component, in combination:
   1. a first bladeless pump structure including means mounting and driving at least one elongated pumping member for rotation about a first axis to cause fluid flow along said axis;
   2. a second bladeless pump structure, in the general form of a hollow cylinder, including means mounting and driving at least one elongated pumping member for rotation about a second axis to cause fluid flow along said axis; and
   3. means mounting said first pumping structure within said second pumping structure so that said first and second axes coincide and said fluid flows are in the same direction.

3. Apparatus according to claim 1 in which said first structure is of greater axial extent than said second structure and projects therebeyond at each end.

4. Apparatus according to claim 3 in which fluid to be pumped by said first structure is supplied thereto at one of the projecting ends and is discharged therefrom at the other projecting end.

5. Apparatus according to claim 1 in which a fluid to be pumped is supplied to each pump structure an one axial end of the axis thereof and is discharged at the other axial end of said axis.

6. Apparatus according to claim 5 in which the direction of fluid movement through said first pump structure is the same as the direction of fluid movement through said second pump structure.

7. Apparatus according to claim 3 in which the mounting and driving means of said first pump structure is contained at least in part in one of the portions thereof which project axially beyond said second pumping structure.

8. Apparatus according to claim 3 in which the mounting and driving means of said first pump structure is contained in the portions thereof that project axially beyond said second pump structure.

9. Apparatus according to claim 1 in which each pump structure includes a pumping member extending axially therealong from an inlet of smaller diameter to an outlet of larger diameter.

10. In rotary pumping apparatus for generating flow with an axial component, in combination:
    1. a first bladeless pump structure including means mounting and driving at least one elongated pumping member for rotation about a first axis to cause fluid flow along said axis;
    2. a second bladeless pump structure, in the general form of a hollow cylinder, including means mounting and driving at least one elongated pumping member for rotation about a second axis to cause fluid flow along said axis; and
    3. means mounting said first pumping structure within said second pumping structure so that said first and second axes coincide and said fluid flows are in the same direction;
    said first structure having an outer surface which increases in diameter from one end toward the other, and said second structure having a central opening of matching configuration which increases in diameter from one end to the other.

* * * * *